(12) United States Patent
Hamamah et al.

(10) Patent No.: US 9,121,066 B2
(45) Date of Patent: Sep. 1, 2015

(54) METHODS FOR SELECTING COMPETENT OOCYTES AND COMPETENT EMBRYOS WITH HIGH POTENTIAL FOR PREGNANCY OUTCOME

(75) Inventors: Samir Hamamah, Montpellier (FR); Said Assou, Montpellier (FR)

(73) Assignees: Institut National de la Sante et de la Recherche Medicale (INSERM), Paris (FR); Universite de Montpellier 1, Montpellier Cedex (FR); Centre Hospitalier Universitaire de Montpellier, Montpellier (FR)

( * ) Notice: Subject to any disclaimer, the term of this patent is extended or adjusted under 35 U.S.C. 154(b) by 83 days.

(21) Appl. No.: 13/989,423

(22) PCT Filed: Nov. 24, 2011

(86) PCT No.: PCT/EP2011/070990
§ 371 (c)(1),
(2), (4) Date: Aug. 6, 2013

(87) PCT Pub. No.: WO2012/069613
PCT Pub. Date: May 31, 2012

(65) Prior Publication Data
US 2013/0316360 A1 Nov. 28, 2013

(30) Foreign Application Priority Data
Nov. 24, 2010 (EP) .................................. 10306293

(51) Int. Cl.
*A61K 31/70* (2006.01)
*C07H 21/02* (2006.01)
*C12Q 1/68* (2006.01)
*C07H 21/04* (2006.01)

(52) U.S. Cl.
CPC ............ *C12Q 1/6876* (2013.01); *C12Q 1/6881* (2013.01); *C12Q 1/6883* (2013.01); *C12N 2310/141* (2013.01); *C12N 2320/10* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2007/0238111 A1   10/2007   Cibelli

FOREIGN PATENT DOCUMENTS

WO       2010/118991 A1   10/2010

OTHER PUBLICATIONS

Database EMBL, "Sequence 456942 from Patent WO2005116250", Jan. 23, 2009, Web.
Database EMBL, "Patent 46 Hairpins Mirs and Binding Sites", Apr. 1, 2010, Web.
Treff et al., "A subset of the cumulus cell transcriptome is predictive of euploid human oocyte reproductive potential", Fertility and Sterility, Sep. 1, 2010, pp. S34-S35, vol. 94, No. 4, Elsevier Science Inc., New York, NY.
Tesfaye et al., "Identification and expression profiling of microRNAs during bovine oocyte maturation using heterologous approach", Molecular Reproduction and Development, Jul. 1, 2009, pp. 665-677, vol. 76, No. 7.
Luense et al., "Role of Dicer in female fertility", Trends in Endocrinology and Metabolism, Aug. 1, 2009, pp. 265-272, vol. 20, No. 6, Elsevier Science Inc., New York, NY.
Zhao et al., "Steroid supplementation during luteal phase influence microRNA expression profiles in the human endometrium after controlled ovarian stimulation with GnRH antagonist protocol", Fertility and Sterility, Sep. 1, 2009, p. S93, vol. 92, No. 3, Elsevier Science Inc., New York, NY.
McCallie et al., "Stability of microRNA in cumulus cells relative to embryo development", Fertility and Sterility, Sep. 1, 2009, p. S252, vol. 92, No. 3, Elsevier Science Inc., New York, NY.
Revel et al., "MicroRNAs are associated with human embryo implantation defects", Human Reproduction, Aug. 16, 2011, pp. 2830-2840, vol. 26, No. 10.
Reich et al., "The Transcriptome of a Human Polar Body Accurately Reflects Its Sibling Oocyte", Journal of Biological Chemistry, Sep. 27, 2011, pp. 40743-40749, vol. 286, No. 47.
Li et al., "MicroRNA array and microarray evaluation of endometrial receptivity in patients with high serum progesterone levels on the day of hCG administration", Reproductive Biology and Endocrinology, Jan. 1, 2011, vol. 9, No. 29.

*Primary Examiner* — Sean McGarry
(74) *Attorney, Agent, or Firm* — Witham Curtis Christofferson & Cook, PC (57) ABSTRACT

The present invention relates to a method for selecting a competent oocyte or a competent embryo by determining the expression level of specific microRNA species in a body fluid or in cumulus cells.

5 Claims, 2 Drawing Sheets

METHODS FOR SELECTING COMPETENT OOCYTES AND COMPETENT EMBRYOS WITH HIGH POTENTIAL FOR PREGNANCY OUTCOME

FIELD OF THE INVENTION

The present invention relates to a method for selecting a competent oocyte or a competent embryo.

BACKGROUND OF THE INVENTION

In assisted reproductive technology (ART), pregnancy and birth rates following in vitro fertilization (IVF) attempts remain low. Indeed, 2 out of 3 IVF cycles fail to result in pregnancy (SART 2004) and more than 8 out of 10 transferred embryos fail to implant (Kovalevsky and Patrizio, 2005). In addition, more than 50% of IVF-born babies are from multiple gestations (Reddy et al., 2007). Preterm deliveries that result from multiple pregnancies caused by ART are estimated to account for approximately $890 million of U.S. health care costs annually (Bromer and Seli, 2008).

The selection of embryos with higher implantation potential has been one of the major challenges in ART. This selection is currently based on morphological criteria such as growth rate, early cleavage on day-1, degree of fragmentation and blastocyst formation (Ebner et al., 2003). However, the predictive power of this approach is still limited. With the emergence of new technologies like 'omics', there are new biomarkers as discovery tools that can be applied to IVF for oocyte and/or embryo selection (Hillier, 2008).

Legal and ethical considerations make biomarkers directly directed to oocytes or embryos difficult to implement. Thus, to avoid any invasive method, some studies have been focused on cumulus cells (CCs).

Indeed, transcriptomic approaches using microarray technology, allowing the simultaneous screening of thousands of genes, were intensively used to identify in CCs the biomarkers related to oocyte competence, which is defined as the intrinsic ability of oocytes to undergo meiotic maturation, fertilization and embryonic development (McKenzie et al., 2004; van Montfoort et al., 2008).

Using the same approach, genes expressed in CCs used as biomarkers associated with embryo quality (McKenzie et al., 2004; van Montfoort et al., 2008; Zhang et al., 2005) and pregnancy outcome (Assou et al., 2008; Hamel et al., 2008; Hamel et al., 2010; Assou et al. 2010) have also been identified.

Even if these studies target the gene expression profile of CCs, a source of cells reflecting the biology and competence of both oocytes and embryos, there is a need to investigate further to develop a non-invasive method of predicting IVF outcome easier to use and with higher reliability.

SUMMARY OF THE INVENTION

The present invention relates to a method for selecting an oocyte that will produce, upon fertilization, a viable embryo with a high implantation rate leading to pregnancy, comprising a step of measuring in a cumulus cell surrounding said oocyte the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

The present invention also relates to a method for selecting an embryo with a high implantation rate leading to pregnancy comprising a step of measuring in a cumulus cell surrounding said embryo the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

The method according to the invention may comprise a further step of measuring in a cumulus cell surrounding said oocyte or said embryo the expression level of one or more genes selected from the group consisting of ATF3, SIAT6, PRKACA, PLA2G5, GPC6, G0S2, RBMS1, NFIC, SLC40A1 and WNT6.

The present invention also relates to a method for selecting an oocyte that will produce, upon fertilization, a viable embryo with a high implantation rate leading to pregnancy, or an embryo with a high implantation rate leading to pregnancy, comprising a step of measuring in a bodily fluid the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:24 and SEQ ID NO: 25.

The present invention also relates to an isolated nucleic acid molecule having the nucleotide sequence as set forth in SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:24 and SEQ ID NO: 25.

DETAILED DESCRIPTION OF THE INVENTION

Definitions

A used herein the term "competent oocyte" refers to a female gamete or egg that when fertilized, i. e. upon fertilization, produces a viable embryo with a high implantation rate leading to pregnancy.

According to the invention, the oocyte may result from a natural cycle, a modified natural cycle or a stimulated cycle for cIVF or ICSI. The term "natural cycle" refers to the natural cycle by which the female or woman produces an oocyte. The term "modified natural cycle" refers to the process by which, the female or woman produces an oocyte or two under a mild ovarian stimulation with GnRH antagonists associated with recombinant FSH or hMG. The term "stimulated cycle" refers to the process by which a female or a woman produces one ore more oocytes under stimulation with GnRH agonists or antagonists associated with recombinant FSH or hMG.

The term "cumulus cell" refers to a cell comprised in a mass of cells that surrounds an oocyte. These cells are believed to be involved in providing an oocyte some of its nutritional, energy and or other requirements that are necessary to yield a viable embryo upon fertilization.

The term "embryo" refers to a fertilized oocyte or zygote. Said fertilization may intervene under a classical in vitro fertilization (cIVF) or under an intracytoplasmic sperm injection (ICSI) protocol.

The term "classical in vitro fertilization" or "cIVF" refers to a process by which oocytes are fertilised by sperm outside of the body, in vitro. IVF is a major treatment in infertility when in vivo conception has failed.

The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm and occasionally as a method of in vitro fertilization, especially that associated with sperm donation.

The term "competent embryo" refers to an embryo with a high implantation rate leading to pregnancy. The term "high implantation rate" means the potential of the embryo when transferred in uterus, to be implanted in the uterine environment and to give rise to a viable foetus, which in turn develops into a viable offspring absent a procedure or event that terminates said pregnancy.

Set of Predictive microRNA

The inventors have identified a set of 42 predictive microRNA according to the invention expressed in cumulus cells and 4 predictive microRNA according to the invention expressed in oocyte.

MicroRNA are single-stranded RNA molecules that regulate the expression of messenger mRNA and play important roles in many physiological processes including growth, differentiation, apoptosis, cell cycle and development (Bushati N, et al. 2007, microRNA functions. Annu Rev Cell Dev Biol 23:175-205). Mature microRNA negatively regulate gene expression by targeting specific messenger mRNA for cleavage or translation repression.

Growing body of evidence suggests that they are involved in the control of a wide range of physiological pathway (Bartel et al., 2009).

It was discovered that some microRNAs circulate in bodily fluid.

These circulating microRNA were found to be usefulness biomarker for diagnosis, prognosis and therapeutics, in particular in cancerology (Kosaka N. et al., 2010).

It was also been discovered than some miRNA can be transferred from a cell to adjacent cells and induce targeted inhibition of protein expression in the acceptor cells (Katakowski M. et al. 2010)

Table I shows the set of predictive microRNA according to the invention.

Some microRNA of the invention are known. They are identified by their name. All information concerning these microRNA, in particular their sequence, can be found on http://www.mirbase.org.

Other microRNA are new. They are identified by their sequence and a sequence identification number (SEQ ID NO) was allocated to each sequences.

TABLE I set of predictive microRNA

| MicroRNA name | MicroRNA nucleotide sequence (only for new microRNA) |
|---|---|
| SEQ ID NO: 6 hsa-mir-103 | AGAAGGAACGUCUGGAGUUUGUGCUGGU |
| SEQ ID NO: 7 | GUUUAUUCUAGAGAGAAUUCUUACUC |
| SEQ ID NO: 8 hsa-mir-1826 | AGACUUUCGGCCUAGGAUC |
| SEQ ID NO: 9 hsa-mir-508 hsa-mir-16 | AGGUUCUGUCGUAUCAAUC |
| SEQ ID NO: 10 hsa-mir-182 hsa-let-7b hsa-let-7c hsa-let-7f hsa-let-7a | CGAGCCGGGCCCUUCCGUC |
| SEQ ID NO: 11 hsa-mir-21 | CGGAAAGGAGGGAAAGGGC |
| SEQ ID NO: 12 hsa-mir-1826 hsa-mir-92a | CGGGCGGAGAGUAGGCAUC |
| SEQ ID NO: 13 | GUGGAGCCGGGCGUGGACU |
| SEQ ID NO: 14 hsa-mir-30d hsa-mir-30a | CUCUUCGUCUGUCCCUAUC |
| SEQ ID NO: 15 | UCCAUCAAAGAUCGGCAUC |
| SEQ ID NO: 16 | UGUGGGAAGAGGGCAUCCU |
| SEQ ID NO: 17 | AGGAGCAAGAGGGCAUCCU |
| SEQ ID NO: 18 | GCGAGGCACUGUGGAGAUC |
| SEQ ID NO: 19 | AGGCAGGUGAAGGCAUCCU |
| SEQ ID NO: 20 | UGGGAUCCCGAGGCAUCCU |
| SEQ ID NO: 21 | GCAGAUCUUCCUGGGUGGUGUGGAC |
| SEQ ID NO: 22 | GGUAGUGUCGCGGGGGUGC (found in oocyte) |
| SEQ ID NO: 23 | AAGGACUGUGAUCAUUGAA (found in oocyte) |
| SEQ ID NO: 24 | AGCGACGUUUCAUUGAAAA (found in oocyte) |
| SEQ ID NO: 25 hsa-mir-1244 hsa-mir-320a | GGGGGCUGUAUCAUUGACA (found in oocyte) |

The inventors have investigated the interaction between these microRNA and mRNA from genes identified to be interesting biomarkers in former studies (McKenzie et al., 2004; van Montfoort et al., 2008; Zhang et al., 2005; Assou et al., 2008; Hamel et al., 2008; Hamel et al., 2010; Assou et al. 2010; WO2010/118991).

MicroRNA of the present invention were found to interact with:
genes whose overexpression is predictive of an oocyte that will produce, upon fertilization, a viable embryo with a high implantation rate leading to pregnancy or an embryo with a high implantation rate leading to pregnancy (group A), genes whose overexpression is predictive of a non competent oocyte or embryo, the embryo being unable to implant (group B), genes whose overexpression is predictive of a non competent oocyte or embryo due to early embryo arrest (group C), genes whose overexpression is inversely correlated with embryo quality (group D), genes whose overexpression is correlated with embryo quality (group E).

Genes are known per se and are identified by their symbol. More information about these genes as sequences or name corresponding to the symbol can be found on Targetscan (http://www.targetscan.org/) and MiRDB (http://mirdb.org/cgi-bin/search.cgi).

Tables A, B, C, D and E show the microRNA contingent to genes with which they interact.

Some microRNA, as hsa-let7a or hsa-mir-182, interact with several genes.

Each table correspond to one group A, B, C, D and E corresponding to specific oocyte or embryo qualities as capacity of an embryo to implant or to develop without arrest as described above.

TABLE A microRNA interacting with genes of group A

| MicroRNA name | Gene symbol | Gene name | Gene ID |
|---|---|---|---|
| hsa-mir-30d | CAMTA1 | calmodulin binding transcription activator 1 | 23261 |
| hsa-mir-30a | CAMTA1 | calmodulin binding transcription activator 1 | 23261 |
| SEQ ID NO: 15 | PCK1 | phosphoenolpyruvate carboxykinase 1 (soluble) | 5105 |
| SEQ ID NO: 16 | PCK1 | phosphoenolpyruvate carboxykinase 1 (soluble) | 5105 |
| SEQ ID NO: 17 | PCK1 | phosphoenolpyruvate carboxykinase 1 (soluble) | 5105 |
| SEQ ID NO: 24 (found in oocyte) | SLAMF6 | SLAM family member 6 | 114836 |

TABLE B microRNA interacting with genes of group B

| MicroRNA name | Gene symbol | Gene name | Gene ID |
|---|---|---|---|
| hsa-mir-182 | EGR3 | early growth response 3 | 1960 |
| hsa-mir-508 | FOSB | FBJ murine osteosarcoma viral oncogene homolog B | 2354 |
| SEQ ID NO: 6 | FOSB | FBJ murine osteosarcoma viral oncogene homolog B | 2354 |
| hsa-let-7a | GPC6 | glypican 6 | 10082 |
| hsa-mir-103 | GPC6 | glypican 6 | 10082 |
| SEQ ID NO: 7 | GPC6 | 'glypican 6 | 10082 |
| SEQ ID NO: 8 | GPC6 | glypican 6 | 10082 |
| hsa-mir-1826 | PDE5A | phosphodiesterase 5A, cGMP-specific | 8654 |
| SEQ ID NO: 9 | PDE5A | phosphodiesterase 5A, cGMP-specific | 8654 |
| hsa-mir-508 | SLC40A1 | solute carrier family 40 (iron-regulated transporter), member 1 | 30061 |

TABLE C microRNA interacting with genes of group C

| MicroRNA name | Gene symbol | Gene name | Gene ID |
|---|---|---|---|
| hsa-mir-16 | G0S2 | G0/G1switch 2 | 50486 |
| SEQ ID NO: 10 | GRIK5 | glutamate receptor, ionotropic, kainate 5 | 2901 |
| hsa-mir-182 | IGF1R | insulin-like growth factor 1 receptor | 3480 |
| hsa-mir-320a | IGF1R | insulin-like growth factor 1 receptor | 3480 |
| hsa-let-7b | IGF1R | insulin-like growth factor 1 receptor | 3480 |
| hsa-let-7c | IGF1R | insulin-like growth factor 1 receptor | 3480 |
| hsa-let-7f | IGF1R | insulin-like growth factor 1 receptor | 3480 |
| hsa-let-7a | IGF1R | insulin-like growth factor 1 receptor | 3480 |
| SEQ ID NO: 11 | IGF1R | insulin-like growth factor 1 receptor | 3480 |
| hsa-mir-21 | NFIB | nuclear factor I/B | 4781 |
| hsa-mir-30d | NFIB | nuclear factor I/B | 4781 |
| hsa-mir-30a | NFIB | nuclear factor I/B | 4781 |
| SEQ ID NO: 12 | NFIC | 'nuclear factor I/C (CCAAT-binding transcription factor) | 4782 |
| SEQ ID NO: 22 (found in oocyte) | NFIC | 'nuclear factor I/C (CCAAT-binding transcription factor) | 4782 |
| hsa-mir-1826 | RBMS1 | RNA binding motif, single stranded interacting protein 1 | 5937 |

TABLE D

MicroRNA interacting with genes of group D

| MicroRNA name | Gene symbol | Gene name | Gene ID |
|---|---|---|---|
| SEQ ID NO: 23 (found in oocyte) | FAT3 | FAT tumor suppressor homolog 3 (Drosophila) | 120114 |
| hsa-mir-92a | SOX4 | SRY (sex determining region Y)-box 4 | 6659 |
| SEQ ID NO: 13 | SOX4 | 'SRY (sex determining region Y)-box 4 | 6659 |
| SEQ ID NO: 14 | SOX4 | 'SRY (sex determining region Y)-box 4 | 6659 |

TABLE E microRNA interacting with genes of group E

| MicroRNA name | Gene symbol | Gene name | Gene ID |
|---|---|---|---|
| SEQ ID NO: 20 (found in oocyte) | EPOR | erythropoietin receptor | 2057 |
| SEQ ID NO: 18 | LRCH4 | leucine-rich repeats and calponin homology (CH) domain containing | 4034 |
| SEQ ID NO: 19 | NLRP1 | NLR family, pyrin domain containing 1 | 22861 |
| SEQ ID NO: 20 | PAX8 | paired box 8 | 7849 |
| SEQ ID NO: 21 | SLC25A5 | solute carrier family 25 (mitochondrial carrier; adenine nucleotide translocator), member 5 | 292 |

TABLE E-continued microRNA interacting with genes of group E

| MicroRNA name | Gene with which the microRNA interacts | | Gene ID |
|---|---|---|---|
| | Gene symbol | Gene name | |
| hsa-mir-1244 | SLC5A12 | solute carrier family 5 (sodium/glucose cotransporter), member 12 | 159963 |
| hsa-mir-320a | SLCO1A2 | solute carrier organic anion transporter family, member 1A2 | 6579 |

Owing to the role of microRNA in post-transcriptional gene regulation, the microRNA of the invention are involved in the regulation of genes listed in tables A, B, C, D and E and subsequently in the associated pregnancy outcome.

An object of the invention relates to a method for selecting an oocyte that will produce, upon fertilization, a viable embryo with a high implantation rate leading to pregnancy, comprising a step of measuring in a cumulus cell surrounding said oocyte the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

The present invention also relates to a method for selecting an embryo with a high implantation rate leading to pregnancy, comprising a step of measuring in a cumulus cell surrounding said embryo the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

Typically, the expression level of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 microRNA may be measured.

In one embodiment, the redundancy is avoided by selecting no more than one microRNA for each gene listed in table A, B, C, D and E.

In one embodiment, the redundancy is avoided by selecting only one or two microRNA by group A, B, C, D or E.

In another embodiment, the methods of the present invention comprises a step of measuring the expression level of at least 5 microRNA selected from the consisting of hsa-mir-103-1, hsa-mir-103-2, hsa-mir-1826, hsa-let-7b, hsa-let-7c, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

In another embodiment, the methods of the present invention comprise a step of measuring the expression level of at least 5 microRNA selected from the group consisting of hsa-mir-508, hsa-mir-16-1, hsa-mir-16-2, hsa-mir-103-1, hsa-mir-103-2, hsa-mir-1974, hsa-mir-1826, SEQ ID NO: 7, SEQ ID NO: 8 and SEQ ID NO: 12.

Indeed, the inventors have shown that these microRNAs present the more significant difference in level of expression between competent oocytes or embryos and oocytes or embryos that are not competent.

In another embodiment, the methods of the present invention comprise a step of measuring the expression level of at least 5 microRNA selected from the group consisting of hsa-mir-508, hsa-mir-16-1, hsa-mir-16-2, hsa-mir-103-1, hsa-mir-103-2, hsa-mir-1974, hsa-mir-1826, SEQ ID NO: 7, SEQ ID NO: 8, SEQ ID NO: 12, hsa-let-7b, hsa-let-7c, hsa-mir-182, hsa-mir-21, hsa-mir-30a and hsa-mir-30d.

Indeed, the inventors have shown that these miRNAs interact with genes particularly relevant in the prediction of the competence of oocytes and embryos such as IGF1R and NFIB.

The present invention also relates to a method for selecting an oocyte that will produce, upon fertilization, a viable embryo with a high implantation rate leading to pregnancy or an embryo with a high implantation rate leading to pregnancy, comprising a step of measuring in a bodily fluid the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:24 and SEQ ID NO: 25.

It is well-known that microRNAs can circulate in bodily fluid.

Thus, Zheng et al. (2011) have shown that hsa-mir-182 is present in plasma and saliva.

Furthermore, Huang et al. (2009), Lawrie et al. (2008), Asaga et al. (2011) and Henegan et al. (2010) have respectively found that hsa-mir-320a, hsa-mir-210, hsa-mir-21 and hsa-let-7a-1 are circulating miRNAs.

Gunel et al. (2011) have shown that increased hsa-mir-210 levels in maternal serum can be used in noninvasive prenatal diagnosis. The expression level of microRNA may be measured in blood, urine, saliva or follicular liquid sample.

The blood sample to be used in the methods according to the invention may be a whole blood sample, a serum sample, or a plasma sample.

The bodily fluid may be taken from the oocyte donor or the host of the embryo.

In one embodiment, the methods of the present invention comprise a step of measuring the expression level of at least 5 microRNAs selected from the group consisting of hsa-mir-182, hsa-mir-320a, hsa-mir-210, hsa-mir-21, hsa-let-7a-1.

The methods of the invention may further comprise a step consisting of comparing the expression level of the microRNA in the sample with a control, wherein detecting differential in the expression level of the microRNA between the sample and the control is indicative whether the oocyte produces, upon fertilization, a viable embryo with a high implantation rate leading to pregnancy or the embryo is with a high implantation rate leading to pregnancy.

The control for oocyte may consist in sample comprising cumulus cells associated with a competent oocyte or a non competent oocyte or in sample comprising cumulus cells associated with an embryo that gives rise to a viable foetus.

Preferably, the control consists in sample comprising cumulus cells associated with a competent oocyte.

The control for embryo may consist in sample comprising cumulus cells associated with an embryo that gives rise to a viable foetus or in a sample comprising cumulus cells associated with an embryo that does not give rise to a viable foetus.

Preferably, the control consists in sample comprising cumulus cells associated with an embryo that gives rise to a viable foetus.

The methods of the invention may further comprise a step of measuring in a cumulus cell surrounding said oocyte or said embryo the expression level of one or more genes selected from the group consisting of ATF3, SIAT6, PRKACA, PLA2G5, GPC6, G0S2, RBMS1, NFIC, SLC40A1 and WNT6.

Typically, the method of the invention may comprise a further step of measuring the expression level of 1, 2, 3, 4, 5, 6, 7, 8, 9 or 10 genes selected from the group consisting of ATF3, SIAT6, PRKACA, PLA2G5, GPC6, G0S2, RBMS1, NFIC, SLC40A1 and WNT6.

Indeed, as described in WO2010/18991, the inventors have identified a set of 45 genes whose measuring the level of expression in cumulus cells is predictive of pregnancy outcome.

After complementary studies, the inventors have determined a subset of 10 genes comprising ATF3, SIAT6, PRKACA, PLA2G5, GPC6, G0S2, RBMS1, NFIC, SLC40A1 and WNT6. This subset appeared to be one of the most reliable set to select an oocyte that will produce, upon fertilization, a viable embryo with a high implantation rate leading to pregnancy or an embryo with a high implantation rate leading to pregnancy in regard of different clinical conditions as shown in Table F.

TABLE F

| Clinical conditions predicted by the set of predictive genes | | |
|---|---|---|
| Gene Symbol | Gene name | Gene ID |
| B: genes whose overexpressions are predictive of embryos unable to implant | | |
| PLA2G5 | phospholipase A2, group V | 5322 |
| GPC6 | glypican 6 | 10082 |
| ATF3 | activating transcription factor 3 | 467 |
| SIAT6 | ST3 beta-galactoside alpha-2,3-sialyltransferase 3 | 6487 |
| PRKACA | protein kinase, cAMP-dependent, catalytic, alpha | 5566 |
| SLC40A1 | solute carrier family 40 (iron-regulated transporter), member 1 | 30061 |
| WNT6 | wingless-type MMTV integration site family, member 6 | 7475 |
| C: genes whose overexpressions are predictive of early embryo arrest | | |
| NFIC | nuclear factor I/C (CCAAT-binding transcription factor) | 4782 |

TABLE F-continued

| Clinical conditions predicted by the set of predictive genes | | |
|---|---|---|
| Gene Symbol | Gene name | Gene ID |
| RBMS1 | RNA binding motif, single stranded interacting protein 1 | 5937 |
| G0S2 | G0/G1 switch 2 | 50486 |

Preferably, genes and microRNA of the present invention aren't measured in a redundant way that is to say that if a microRNA is selected, the gene with which it interacts won't be selected.

In one embodiment, to avoid any redundancy, the method of the invention may comprise a further step of measuring the expression level of 1 or 2 genes selected from group B and 1 or 2 genes selected from group C.

Alternatively, said one or more genes may be selected for example from group B alone or group C alone.

Typically, 1, 2, 3, 4, 5, 6 or 7 genes may be selected from group B.

Typically, 1, 2 or 3 genes may be selected from group C.

The present invention also relates to a method for selecting an oocyte that will produce, upon fertilization, a viable embryo with a high implantation rate leading to pregnancy or an embryo with a high implantation rate leading to pregnancy, comprising a step of measuring in the culture medium of cumulus cell having surrounded said oocyte or said embryo the expression level of at least 5 microRNA selected from the group consisting of hsa-mir-103-1, hsa-mir-103-2, hsa-mir-1826, hsa-let-7a-1, hsa-let-7a-2, hsa-let-7a-3, hsa-let-7b, hsa-let-7c, hsa-let-7f, hsa-mir-1244, hsa-mir-182, hsa-mir-21, hsa-mir-30a, hsa-mir-30d, hsa-mir-320a, hsa-mir-508, hsa-mir-92a-1, hsa-mir-92a-2, hsa-mir-16-1, hsa-mir-16-2, hsa-mir-1974, hsa-mir-146b, hsa-mir-886, hsa-mir-210, hsa-mir-1979, hsa-mir-125a, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

The methods of the invention are particularly suitable for assessing the efficacy of an in vitro fertilization treatment. Accordingly the invention also relates to a method for assessing the efficacy of a controlled ovarian hyperstimulation (COS) protocol in a female subject comprising:

i) providing from said female subject at least one oocyte with its cumulus cells;

ii) determining by a method of the invention whether said oocyte is an oocyte that will produce, upon fertilization, a viable embryo with a high implantation rate leading to pregnancy e.

Then after such a method, the embryologist may select the oocytes that will produce, upon fertilization, a viable embryo with a high implantation rate leading to pregnancy and in vitro fertilized them through a classical in vitro fertilization (cIVF) protocol or under an intracytoplasmic sperm injection (ICSI) protocol.

A further object of the invention relates to a method for monitoring the efficacy of a controlled ovarian hyperstimulation (COS) protocol comprising:

i) isolating from said woman at least one oocyte with its cumulus cells under natural, modified or stimulated cycles;

ii) determining by a method of the invention whether said oocyte is an oocyte that will produce, upon fertilization, a viable embryo with a high implantation rate leading to pregnancy;

iii) and monitoring the efficacy of COS treatment based on whether it results in an oocyte that will produce, upon fertilization, a viable embryo with a high implantation rate leading to pregnancy.

The COS treatment may be based on at least one active ingredient selected from the group consisting of GnRH agonists or antagonists associated with recombinant FSH or hMG.

The present invention also relates to a method for determining whether an embryo is an embryo with a high implantation rate leading to pregnancy, comprising:
i) providing an oocyte with its cumulus cells
ii) in vitro fertilizing said oocyte
iii) determining whether the embryo that results from step ii) has a high implantation rate leading to pregnancy by determining by a method of the invention whether said oocyte of step i), is an oocyte that will produce, upon fertilization, a viable embryo with a high implantation rate leading to pregnancy.

The methods of the invention are particularly suitable for enhancing the pregnancy outcome of a female. Accordingly the invention also relates to a method for enhancing the pregnancy outcome of a female comprising:
i) selecting an embryo with a high implantation rate leading to pregnancy by performing a method of the invention
iii) implanting the embryo selected at step i) in the uterus of said female.

The method as above described will thus help embryologist to avoid the transfer in uterus of embryos with a poor potential for pregnancy out come.

The method as above described is also particularly suitable for avoiding multiple pregnancies by selecting the competent embryo able to lead to an implantation and a pregnancy.

The invention also relates to a kit for performing the methods as above described, wherein said kit comprises means for measuring the expression level of the microRNA of Table I that are indicative whether the oocyte that will produce, upon fertilization, a viable embryo with a high implantation rate leading to pregnancy or the embryo with a high implantation rate leading to pregnancy.

It is to note that the methods of the invention leads to an independence from morphological considerations of the embryo. Two embryos may have the same morphological aspects but by a method of the invention may present a different implantation rate leading to pregnancy.

The methods of the invention are applicable preferably to women but may be applicable to other mammals (e.g., primates, dogs, cats, pigs, cows . . . ).

The present invention also relates to an isolated nucleic acid molecule having the nucleotide sequence as set forth in SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:24 and SEQ ID NO: 25.

In one embodiment, the nucleic acid molecule according to the invention is used in diagnosis of infertility.

The present invention also relates to a method for the diagnosis of infertility comprising the step of measuring the expression level of at least 5 microRNA selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:24 and SEQ ID NO: 25.

The invention will be further illustrated by the following figures and examples. However, these examples and figures should not be interpreted in any way as limiting the scope of the present invention.

Figure 1:
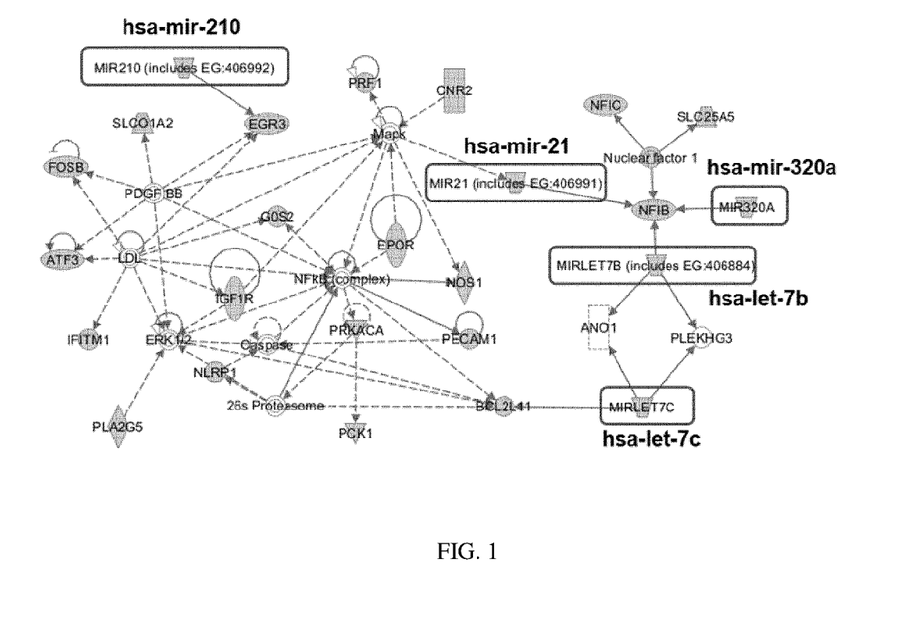
FIGS. 1 to 4 are diagrams illustrating molecular pathways and functional groupings between microRNA and biomarkers genes.
Figure 2:
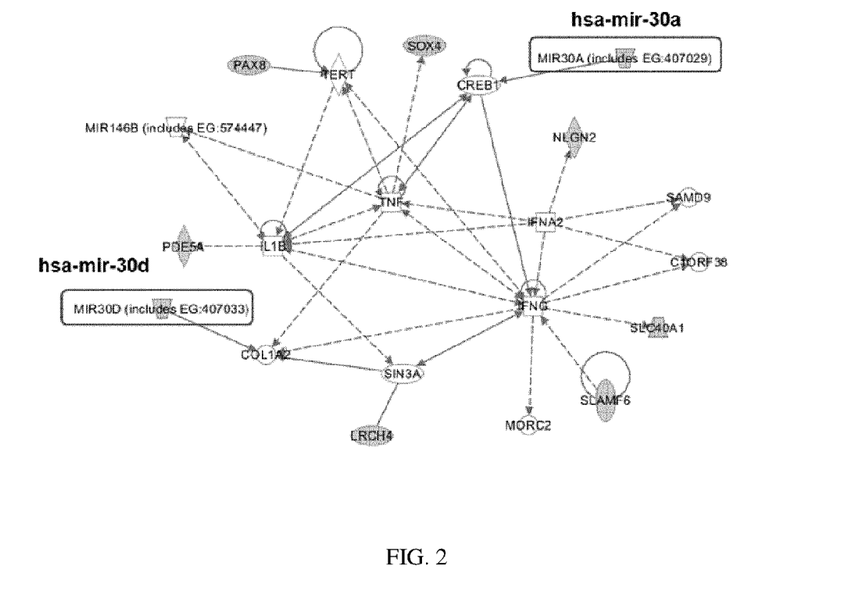
Figure 3:
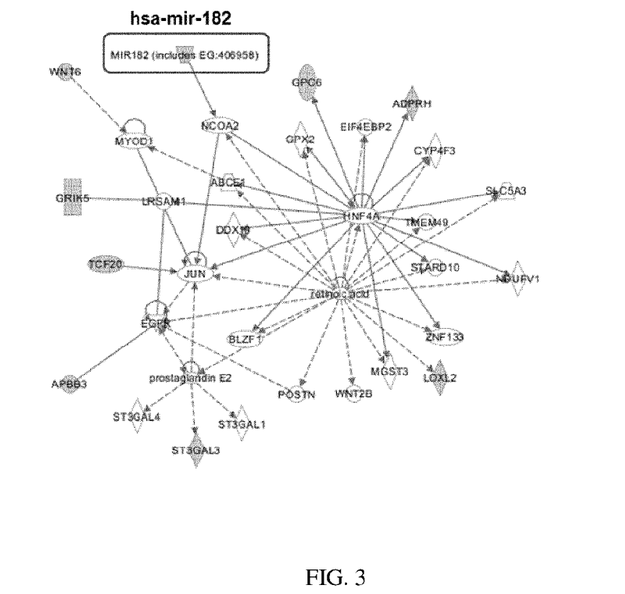
Figure 4:
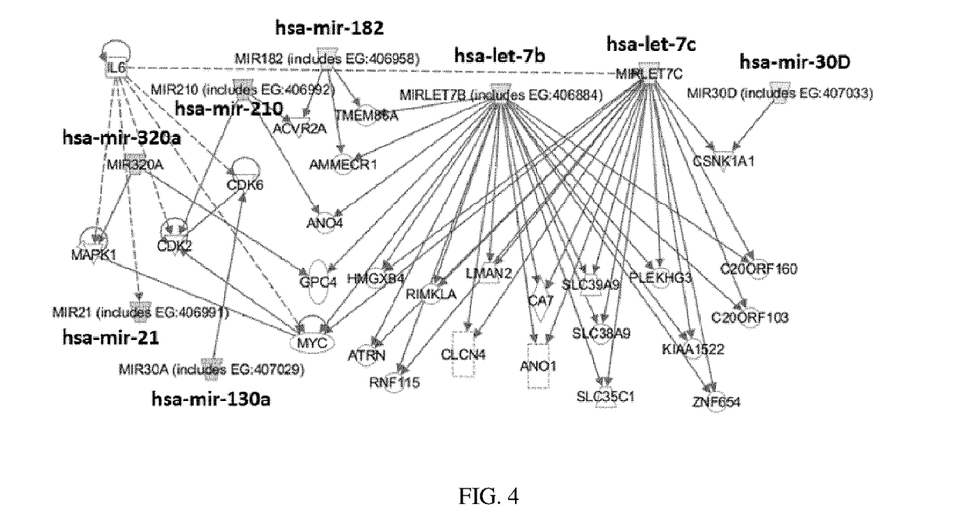

These diagrams were done by using the Ingenuity Pathways Analysis (IPA) system (Ingenuity Systems, Redwood City, Calif., USA) thank to published literature related to above mentioned miRNA and genes. Above mentioned miRNA and genes were uploaded into IPA and overlaid onto a global molecular network developed from information contained in the application. Networks of these miRNA and genes were generated by IPA based on their connectivity (FIG. 1 to 4). The biological relationship between two nodes is represented as an edge (line). All lines are supported by at least one reference in literature, textbook, or from canonical information stored in the Ingenuity Pathways knowledge database.

Example

Samples: Cumulus cells and mature MII oocytes were collected from patients consulting for conventional IVF (cIVF) or for ICSI (male infertility). Cumulus cells were removed from a mature oocyte (MII). CCs were partially separated mechanically from the corresponding oocyte as previously described (Assou et al., 2008). Unfertilized MII oocytes were collected 21 or 44 h after insemination or after microinjection by ICSI. Cumulus cells and oocytes were frozen at −80° C. in RLT buffer (RNeasy Kit, Qiagen, Valencia, Calif.) before miRNA extraction.

Methods for Determining the Expression Level of the microRNA:

Determination of the expression level of the microRNA can be performed by a variety of techniques known in the art.

Preferably, small RNA from cumulus cells and mature MII oocyte samples was extracted after storage of samples at −80° C. in RLT RNA extraction buffer supplemented with 1 µM of 2-β-mercaptoethanol (M-3148, Sigma) as described in the manufacturer's protocol (miRNeasy mini Kit, Qiagen, Valencia, Calif.).

The 5' RNA adapter (5'-GUUCAGAGUUCUACAGUC-CGACGAUC-3' (SEQ ID NO: 1)) was ligated to the RNA pool with T4 RNA ligase (Ambion) in the presence of RNase Out (Invitrogen) overnight at 25° C. The ligation reaction was stopped by the addition of 2× formamide loading dye. The ligated RNA was size fractionated on a 15% TBE urea polyacrylamide gel and a 40-60 base pair fraction was excised. RNA was eluted from the polyacrylamide gel slice in 600 µL of 0.3 M NaCl overnight at 4° C. The RNA was eluted from the gel and precipitated as described above followed by resuspension in DEPC-treated water.

The 3' RNA adapter ((SEQ ID NO: 2) 5'-pUCGUAUGC-CGUCUUCUGCUUGidT-3'; p, phosphate; idT, inverted deoxythymidine) was subsequently ligated to the precipitated RNA with T4 RNA ligase (Ambion) in the presence of RNase Out (Invitrogen) overnight at 25° C. The ligation reaction was stopped by the addition of 10 µL of 2× formamide loading dye. Ligated RNA was size fractionated on a 10% TBE urea polyacrylamide gel and the 60-100 base pair fraction was excised. The RNA was eluted from the polyacrylamide gel and precipitated from the gel as described above and resuspended in 5.0 µL of DEPC water. The RNA was converted to single-stranded cDNA using Superscript II reverse transcriptase (Invitrogen) and Illumina's small RNA RT-Primer (5'-CAAGCAGAAGACGGCATACGA-3' (SEQ ID NO: 3)) following the manufacturer's instructions. The resulting cDNA was PCR-amplified with Hotstart Phusion DNA Polymerase (NEB) in 15 cycles using 15 cycles using Illumina's small RNA primer set (5'-CAAGCAGAAGACG GCATACGA-3' (SEQ ID NO: 4); 5'-AATGATACGGCGACCAC-CGA-3' (SEQ ID NO: 5)).

PCR products were purified on a 12% TBE urea polyacrylamide gel and eluted into elution buffer (5:1, LoTE: 7.5 M ammonium acetate) overnight at 4° C. The resulting gel slurry was passed through a Spin-X filter (Corning) and precipitated by the addition of 1100 µL of ethanol, 133 µL of 7.5 M ammonium acetate and 3 µL of mussel glycogen (20 mg/mL; Invitrogen). After washing with 75% ethanol, the pellet was allowed to air dry at 25° C. and dissolved in EB buffer (Qiagen) by incubation at 4° C. for 10 min. The purified PCR products were quantified on the Agilent DNA 1000 chip and diluted to 10 nM for sequencing on the Illumina 1G.

Small RNA Annotation

We trimmed all reads at 30 nt to reduce the number of unique sequences. We counted the occurrences of each unique sequence read and used only the unique sequences for further analysis. All sequence tags are mapped onto the human reference genome using the SOAP program following the mirTools web server procedure (Zhu E L, Zhao F Q, et al., NAR 2010). Subsequently, these unique sequence tags are also aligned against miRBase (Griffiths-Jones, S et al. NAR 2008), Rfam (Griffiths-Jones, S et al, NAR 2005), repeat database produced by RepeatMasker (Tarailo-Graovac, M. and Chen, N. (2009) Curr. Protoc. Bioinform., Chapter 4, Unit 4. 108.) and the coding genes of the reference genome. In this way, the unique sequence tags can be classified into the following categories: known microRNA, degradation fragments of non-coding RNA, genomic repeats and mRNA. In case of conflict, a hierarchy is conducted to assign the tag into a unique category, which starts with non-coding RNA, then known microRNA and followed by repeat associated RNA and mRNA. Sequences that are assigned to none of these annotations but can be mapped to the reference genome are classified as 'unclassified'.

A microRNA target prediction were done using known microRNA and TargetScan data (release 4.0) which provides predicted targets for known microRNAs (http://www.targetscan.org/).

Differential Expression Detection

To compare differentially expressed microRNA between multiple samples, read count of each identified microRNA is normalized to the total number of microRNA read counts that are matched to the reference genome in each sample. The statistical significance (P-value) is inferred based on a Bayesian method (Audic, S. and Claverie, J. M. (1997) Genome Res.), which was developed for analyzing digital gene expression profiles and could account for the sampling variability of tags with low counts. In default, a specific microRNA will be deemed to be significantly differentially expressed when the P-value given by this method is 0.01 and there is at least a 2-fold change in normalized sequence counts.

Novel microRNA Prediction

Sequences that do not fall into above annotation categories but matched on the reference genome are used to detect candidate novel microRNA genes. In default, 100 nucleotides of genomic sequence flanking each side of these sequences are extracted and their RNA secondary structures are predicted using RNAfold (Hofacker, I. L. NAR 2003). Novel microRNAs are identified by folding the flanking genomic sequence using the miRDeep program.

Methods for Determining the Expression Level of the Genes:

Determination of the expression level of genes as ATF3, SIAT6, PRKACA, PLA2G5, GPC6, G0S2, RBMS1, NFIC, SLC40A1 or WNT6 can be performed by a variety of techniques. Generally, the expression level as determined is a relative expression level.

Some of these methods are well described in WO2010/118991.

Results

Analysis of level of expression of microRNA in CCs has permitted to identify candidate microRNA biomarkers.

Known microRNA

Known microRNA from CCs group are listed in Table G.

TABLE G

Set of known predicitve microRNA:

| microRNAs | Length | startend | location | e_value |
|---|---|---|---|---|
| hsa-mir-1974 | 26 | 1 ... 26 | 45 ... 70 | 2.00E−10 |
| hsa-let-7b | 18 | 1 ... 18 | 6 ... 23 | 7.00E−06 |
| hsa-mir-1244 | 22 | 1 ... 22 | 57 ... 78 | 4.00E−08 |
| hsa-mir-30d | 24 | 1 ... 24 | 6 ... 29 | 3.00E−09 |
| hsa-mir-182 | 19 | 1 ... 19 | 28 ... 46 | 2.00E−06 |
| hsa-mir-146b | 24 | 1 ... 24 | 9 ... 32 | 3.00E−09 |
| hsa-let-7c | 19 | 1 ... 19 | 11 ... 29 | 2.00E−06 |
| hsa-mir-92a-2 | 22 | 1 ... 22 | 48 ... 69 | 4.00E−08 |
| hsa-mir-92a-1 | 22 | 1 ... 22 | 48 ... 69 | 4.00E−08 |
| hsa-mir-886 | 25 | 1 ... 25 | 15 ... 39 | 7.00E−10 |
| hsa-mir-508 | 22 | 1 ... 22 | 61 ... 82 | 4.00E−08 |
| hsa-mir-320a | 18 | 1 ... 18 | 52 ... 69 | 7.00E−06 |
| hsa-mir-30a | 24 | 1 ... 24 | 6 ... 29 | 3.00E−09 |
| hsa-mir-210 | 19 | 1 ... 19 | 66 ... 84 | 2.00E−06 |
| hsa-mir-21 | 22 | 1 ... 22 | 9 ... 30 | 4.00E−08 |
| hsa-mir-1979 | 24 | 1 ... 24 | 6 ... 29 | 3.00E−09 |
| hsa-mir-1826 | 24 | 1 ... 24 | 1 ... 24 | 3.00E−09 |
| hsa-mir-16-2 | 19 | 1 ... 19 | 10 ... 28 | 2.00E−06 |
| hsa-mir-16-1 | 19 | 1 ... 19 | 14 ... 32 | 2.00E−06 |
| hsa-mir-125a | 24 | 1 ... 24 | 15 ... 38 | 3.00E−09 |
| hsa-mir-103-2 | 22 | 1 ... 22 | 48 ... 69 | 4.00E−08 |
| hsa-mir-103-1 | 22 | 1 ... 22 | 48 ... 69 | 4.00E−08 |
| hsa-let-7a-3 | 20 | 1 ... 20 | 4 ... 23 | 5.00E−07 |
| hsa-let-7a-2 | 20 | 1 ... 20 | 5 ... 24 | 5.00E−07 |
| hsa-let-7a-1 | 20 | 1 ... 20 | 6 ... 25 | 5.00E−07 |
| hsa-let-7f | 22 | 1 ... 22 | 7 ... 28 | 4.00E−07 |

The interaction between these microRNA and mRNA from gene identified to be potential biomarkers by the inventors (WO2010/118991, Assou et al., 2008; Assour et al. 2010) was studied by using TargetScan.

TargetScan predicts biological targets of miRNAs by searching for the presence of conserved 8 mer and 7 mer sites that match the seed region of each miRNA (Lewis et al., 2005). As an option, nonconserved sites are also predicted. Also identified are sites with mismatches in the seed region that are compensated by conserved 3' pairing (Friedman et al., 2009). In mammals, predictions are ranked based on the predicted efficacy of targeting as calculated using the context scores of the sites (Grimson et al., 2007). TargetScanHuman considers matches to annotated human UTRs and their orthologs, as defined by UCSC whole-genome alignments. Conserved targeting has also been detected within open reading frames (ORFs).

Other database as MiRDB (http://mirdb.org/cgi-bin/search.cgi) and Ingenuity (IPA) have also been used.

Some of these interactions are illustrated in FIGS. 1 to 4.

New microRNA Biomarkers

The inventors have identified novel microRNA among the unclassified sequences in their libraries. After annotation, 5,165 of the microRNA sequences in the CCs library remained unclassified because they derived from unannotated regions of the human genome. Novel microRNA were identified. These microRNA regulate the expression of 7 gene biomarkers such as: (PCK1 (3 microRNA: SEQ ID NO: 15; SEQ ID NO: 16; SEQ ID NO: 17); GPC6 (2 microRNA: SEQ ID NO: 7, SEQ ID NO: 8); SOX4 (2 microRNA: SEQ ID NO: 13, SEQ ID NO: 14); SLC25A5 (1 microRNA: SEQ ID NO: 21); NFIC (1 microRNA: SEQ ID NO: 12; SEQ ID NO: 22); IGF1R (1 microRNA: SEQ ID NO: 11); GIRK5 (1 microRNA: SEQ ID NO: 10)).

Interactions microARN and Genes Identified to be Interesting Biomarkers

The inventors have investigated the interaction between these microRNA and mRNA from genes identified to be interesting biomarkers in former studies (McKenzie et al., 2004; van Montfoort et al., 2008; Zhang et al., 2005; Assou et al., 2008; Hamel et al., 2008; Hamel et al., 2010; Assou et al. 2010; WO2010/118991).

MiRNA are known to be post-transcriptional regulators that bind to complementary sequences on target messenger RNA transcripts (mRNAs), usually resulting in translational repression or target degradation and gene silencing (Bartel et D P (2009)).

Thus, without being bound by theory, the under-expression of most microRNA that interact with a gene whose overexpression is predictive of a competent oocyte or a competent embryo is predictive of an oocyte that will produce, upon fertilization, a viable embryo with a high implantation rate leading to pregnancy or of an embryo with a high implantation rate leading to pregnancy.

In the same way, the under-expression of most microRNA that interact with a gene whose overexpression is predictive of an oocyte or an embryo that is not competent is predictive of an oocyte or an embryo that is not competent.

For example, SEQ ID NO: 23, hsa-mir-92a, SEQ ID NO: 13 and SEQ ID NO: 14 interact with genes of group D. Thus, their under-expression can be predictive of a bad quality embryo.

Conversely, the overexpression of most microRNA that interact with a gene whose under-expression is predictive of a competent oocyte or a competent embryo is predictive of an oocyte that will produce, upon fertilization, a viable embryo with a high implantation rate leading to pregnancy or of an embryo with a high implantation rate leading to pregnancy.

By extension, the overexpression of most miRNA that interact with a gene whose overexpression is predictive of an embryo unable to implant, early embryo arrest or a bad quality embryo is predictive of an oocyte that will produce, upon fertilization, a viable embryo with a high implantation rate leading to pregnancy or of an embryo with a high implantation rate leading to pregnancy.

For example, overexpression of a miRNA interacting with genes of groups B, C and D can be predictive of an oocyte that will produce, upon fertilization, a viable embryo with a high implantation rate leading to pregnancy or of an embryo with a high implantation rate leading to pregnancy when it is under-expressed.

CONCLUSION

CC gene and microRNA expression analysis begins to be a valuable tool for improving embryo selection, either for fresh embryo replacement or for freezing. According to our preliminary data, there is no relationship between the gene expression profile of CCs and the embryo morphological aspects. It is time to reconsider the notion that embryos presenting a low grade according morphological aspects are able to achieve pregnancy. Indeed, during the last decade, the availability of technical platforms, small RNA library sequencing and whole genome microarrays has rapidly generated data on the molecular mechanisms of the CC-oocyte complex. Today, these technologies provide potential predictive biomarkers as non-invasive tools for clinical applications. Finally, this concept reveals the potential of CCs microRNA to serve as molecular biomarkers for embryo selection.

REFERENCES

Throughout this application, various references describe the state of the art to which this invention pertains. The disclosures of these references are hereby incorporated by reference into the present disclosure.

Asaga S, Kuo C, Nguyen T, Terpenning M, Giuliano A E, Hoon D S. (2011) Direct serum assay for microRNA-21 concentrations in early and advanced breast cancer. Clin Chem. 2011 January; 57(1):84-91. Epub 2010 Oct. 29.

Assou, S., Anahory, T., Pantesco, V., Le Carrour, T., Pellestor, F., Klein, B., Reyftmann, L., Dechaud, H., De Vos, J., Hamamah, S. (2006) The human cumulus—oocyte complex gene-expression profile. Hum Reprod, 21, 1705-19.

Assou S., Haouzi D., Mahmoud K., Aouacheria A., Guillemin Y., Pantesco V., Reme T., Dechaud H., De vos J., Hamamah S. (2008) A non invasive test for assessing embryo potential by gene expression profiles of human cumulus cells: a proof of concept study. Molecular human reproduction, Vol. 14, no 12 pp. 711-719, December 2008.

Balaban, B., Urman, B. (2006) Effect of oocyte morphology on embryo development and implantation. Reprod Biomed Online, 12, 608-15.

Bartel et D P. 2009. MicroRNAs: genomics, biogenesis mechanism and function. Cell, 136:215-233.

Brison, D. R., Houghton, F. D., Falconer, D., Roberts, S. A., Hawkhead, J., Humpherson, P. G., Lieberman, B. A., Leese, H. J. (2004) Identification of viable embryos in IVF by non-invasive measurement of amino acid turnover. Hum Reprod, 19, 2319-24.

Bromer, J. G., Seli, E. (2008) Assessment of embryo viability in assisted reproductive technology: shortcomings of current approaches and the emerging role of metabolomics. Curr Opin Obstet Gynecol, 20, 234-41.

Courtois, G., Smahi, A. (2006) NF-kappaB-related genetic diseases. Cell Death Differ, 13, 843-51.

de Hoon, M. J., Imoto, S., Nolan, J., Miyano, S. (2004) Open source clustering software. Bioinformatics, 20, 1453-4.

Ebner T, Moser M, Sommergruber M, Gaiswinkler U, Wiesinger R, Puchner M, Tews G., (2003) Presence, but not type or degree of extension, of a cytoplasmic halo has a significant influence on preimplantation development and implantation behaviour, Hum Reprod. 2003 November; 18(11):2406-12.

Eisen, M. B., Spellman, P. T., Brown, P. O., Botstein, D. (1998) Cluster analysis and display of genome-wide expression patterns. Proc Natl Acad Sci USA, 95, 14863-8.

Fenwick, J., Platteau, P., Murdoch, A. P., Herbert, M. (2002) Time from insemination to first cleavage predicts developmental competence of human preimplantation embryos in vitro. Hum Reprod, 17, 407-12.

Feuerstein, P., Cadoret, V., Dalbies-Tran, R., Guerif, F., Bidault, R., Royere, D. (2007) Gene expression in human cumulus cells: one approach to oocyte competence. Hum Reprod, 22, 3069-77.

Fourar M., Haouzi D., Aouacheria A., Dechaud h., Bendhaou k., Hamamah S. (2008) Gene expression profiles of human cumulus cells and pregnancy outcome: identification of molecular biomarkers of embryo competence, Fertility and Sterility, vol. 90, 1 Sep. 2008, p. S72, Abstract.

Robin C Friedman, Kyle Kai-How Farh, Christopher B Burge, David P Bartel. Most Mammalian mRNAs Are Conserved Targets of MicroRNAs Genome Research, 19:92-105 (2009).

Gardner, D. K., Lane, M., Stevens, J., Schoolcraft, W. B. (2001) Noninvasive assessment of human embryo nutrient consumption as a measure of developmental potential. Fertil Steril, 76, 1175-80.

Gasca, S., Pellestor, F., Assou, S., Loup, V., Anahory, T., Dechaud, H., De Vos, J., Hamamah, S. (2007) Identifying new human oocyte marker genes: a microarray approach. Reprod Biomed Online, 14, 175-83.

Andrew Grimson, Kyle Kai-How Farh, Wendy K Johnston, Philip Garrett-Engele, Lee P Lim, David P Bartel. MicroRNA Targeting Specificity in Mammals: Determinants beyond Seed Pairing Molecular Cell, 27:91-105 (2007)

Hamel, M., Dufort, I., Robert, C., Gravel, C., Leveille, M. C., Leader, A., Sirard, M. A. (2008) Identification of differentially expressed markers in human follicular cells associated with competent oocytes. Hum Reprod, 23, 1118-27.

Haouzi, D., De Vos, J., Loup, V., Assou, S., Gasca, S., Reyftmann, L., Klein, B., Hamamah, S. (2008) [Oocyte and embryo quality: Do the apoptotic markers have a place in the preimplantation genetic diagnostic?]. Gynecol Obstet Fertil, 36, 730-742.

He, B., Chadburn, A., Jou, E., Schattner, E. J., Knowles, D. M., Cerutti, A. (2004) Lymphoma B cells evade apoptosis through the TNF family members BAFF/BLyS and APRIL. J Immunol, 172, 3268-79.

Hamel M, Dufort I, Robert C, Léveillé Leader A, Sirard M A (2010), Identification of follicular marker genes as pregnancy predictors for human IVF: new evidence for the involvement of luteinization process; Mol Hum Reprod. 2010 August; 16(8):548-56. Epub 2010 Jul. 7.

Heneghan H M, Miller N, Lowery A J, Sweeney K J, Newell J, Kerin M J. (2010) Circulating microRNAs as novel minimally invasive biomarkers for breast cancer. Ann Surg. 2010 March; 251(3):499-505.

Hillier S G., (2008) Research challenge: what is the best non-invasive test of oocyte/embryo competence?; Mol Hum Reprod. 2008 December; 14(12):665. Epub 2008 Nov. 20.

Huang Z, Huang D, Ni S, Peng Z, Sheng W, Du X. (2010) Plasma microRNAs are promising novel biomarkers for early detection of colorectal cancer. Int J Cancer. 2010 Jul. 1; 127(1):118-26.

Katakowski M, Buller B, Wang X, Rogers T, Chopp M., (2010) Functional microRNA is transferred between glioma cells. Cancer Res. 2010 Nov. 1; 70(21):8259-63. Epub 2010 Sep. 14.

Kolena, J., Kiss, A., Channing, C. P. (1983) Purification of porcine granulosa cells by continuous Percoll gradient. Experientia, 39, 908-9.

Kosaka N, Iguchi H, Ochiya T. (2010) Circulating microRNA in body fluid: a new potential biomarker for cancer diagnosis and prognosis, Cancer Sci. 2010 October 101(10): 2087-92.

Kovalevsky, G., Patrizio, P. (2005) High rates of embryo wastage with use of assisted reproductive technology: a look at the trends between 1995 and 2001 in the United States. Fertil Steril, 84, 325-30.

La Sala, G. B., Nicoli, A., Villani, M. T., Di Girolamo, R., Capodanno, F., Blickstein, I. (2008) The effect of selecting oocytes for insemination and transferring all resultant embryos without selection on outcomes of assisted reproduction. Fertil Steril.

Lawrie C H, Gal S, Dunlop H M, Pushkaran B, Liggins A P, Pulford K, Banham A H, Pezzella F, Boultwood J, Wainscoat J S, Hatton C S, Harris A L. (2008) Detection of elevated levels of tumour-associated microRNAs in serum of patients with diffuse large B-cell lymphoma. Br J Haematol. 2008 May; 141(5):672-5. Epub 2008 Mar. 3.

Lee, K. S., Joo, B. S., Na, Y. J., Yoon, M. S., Choi, O. H., Kim, W. W. (2001) Cumulus cells apoptosis as an indicator to predict the quality of oocytes and the outcome of IVF-ET. J Assist Reprod Genet, 18, 490-8.

Benjamin P Lewis, Christopher B Burge, David P Bartel. Conserved Seed Pairing, Often Flanked by Adenosines, Indicates that Thousands of Human Genes are MicroRNA Targets Cell, 120:15-20 (2005).

Lundin, K., Bergh, C., Hardarson, T. (2001) Early embryo cleavage is a strong indicator of embryo quality in human IVF. Hum Reprod, 16, 2652-7.

McKenzie, L. J., Pangas, S. A., Carson, S. A., Kovanci, E., Cisneros, P., Buster, J. E., Amato, P., Matzuk, M. M. (2004) Human cumulus granulosa cell gene expression: a predictor of fertilization and embryo selection in women undergoing IVF. Hum Reprod, 19, 2869-74.

Pearson, H. (2006) Safer embryo tests could boost IVF pregnancy rates. Nature, 444, 12-3.

Perlman, S., Bouquin, T., van den Hazel, B., Jensen, T. H., Schambye, H. T., Knudsen, S., Okkels, J. S. (2006) Transcriptome analysis of FSH and FSH variant stimulation in granulosa cells from IVM patients reveals novel regulated genes. Mol Hum Reprod, 12, 135-44.

Reddy, U. M., Wapner, R. J., Rebar, R. W., Tasca, R. J. (2007) Infertility, assisted reproductive technology and adverse pregnancy outcomes: executive summary of a National Institute of Child Health and Human Development workshop. Obstet Gynecol, 109, 967-77.

Reme, T., Hose, D., De Vos, J., Vassal, A., Poulain, P. O., Pantesco, V., Goldschmidt, H., Klein, B. (2008) A new method for class prediction based on signed-rank algorithms applied to Affymetrix microarray experiments. BMC Bioinformatics, 9, 16.

Sakkas, D., Gardner, D. K. (2005) Noninvasive methods to assess embryo quality. Curr Opin Obstet Gynecol, 17, 283-8.

Sasson, R., Dantes, A., Tajima, K., Amsterdam, A. (2003) Novel genes modulated by FSH in normal and immortalized FSH-responsive cells: new insights into the mechanism of FSH action. Faseb J, 17, 1256-66.

Sasson, R., Rimon, E., Dantes, A., Cohen, T., Shinder, V., Land-Bracha, A., Amsterdam, A. (2004) Gonadotrophin-induced gene regulation in human granulosa cells obtained from IVF patients. Modulation of steroidogenic genes, cytoskeletal genes and genes coding for apoptotic signalling and protein kinases. Mol Hum Reprod, 10, 299-311.

Scott, L., Alvero, R., Leondires, M., Miller, B. (2000) The morphology of human pronuclear embryos is positively related to blastocyst development and implantation. Hum Reprod, 15, 2394-403.

Seli, E., Sakkas, D., Scott, R., Kwok, S. C., Rosendahl, S. M., Burns, D. H. (2007) Noninvasive metabolomic profiling of embryo culture media using Raman and near-infrared spectroscopy correlates with reproductive potential of embryos in women undergoing in vitro fertilization. Fertil Steril, 88, 1350-7.

Steele-Perkins, G., Plachez, C., Butz, K. G., Yang, G., Bachurski, C. J., Kinsman, S. L., Litwack, E. D., Richards, L. J., Gronostajski, R. M. (2005) The transcription factor gene Nfib is essential for both lung maturation and brain development. Mol Cell Biol, 25, 685-98.

Stein, J. V., Lopez-Fraga, M., Elustondo, F. A., Carvalho-Pinto, C. E., Rodriguez, D., Gomez-Caro, R., De Jong, J., Martinez, A. C., Medema, J. P., Hahne, M. (2002) April modulates B and T cell immunity. J Clin Invest, 109, 1587-98.

Su, Y. Q., Sugiura, K., Wigglesworth, K., O'Brien, M. J., Affourtit, J. P., Pangas, S. A., Matzuk, M. M., Eppig, J. J. (2008) Oocyte regulation of metabolic cooperativity between mouse cumulus cells and oocytes: BMP15 and GDF9 control cholesterol biosynthesis in cumulus cells. Development, 135, 111-21.

Sugiura, K., Su, Y. Q., Diaz, F. J., Pangas, S. A., Sharma, S., Wigglesworth, K., O'Brien, M. J., Matzuk, M. M., Shimasaki, S., Eppig, J. J. (2007) Oocyte-derived BMP15 and FGFs cooperate to promote glycolysis in cumulus cells. Development, 134, 2593-603.

Tusher, V. G., Tibshirani, R., Chu, G. (2001) Significance analysis of microarrays applied to the ionizing radiation response. Proc Natl Acad Sci USA, 98, 5116-21.

Van Montfoort, A. P., Dumoulin, J. C., Kester, A. D., Evers, J. L. (2004) Early cleavage is a valuable addition to existing embryo selection parameters: a study using single embryo transfers. Hum Reprod, 19, 2103-8.

van Montfoort, A. P., Geraedts, J. P., Dumoulin, J. C., Stassen, A. P., Evers, J. L., Ayoubi, T. A. (2008) Differential gene expression in cumulus cells as a prognostic indicator of embryo viability: a microarray analysis. Mol Hum Reprod, 14, 157-68.

Yang, W. J., Hwu, Y. M., Lee, R. K., Li, S. H., Lin, S. Y., Fleming, S. (2007) Early cleavage does not predict treatment outcome following the use of GnRH antagonists in women older than 35. Fertil Steril, 88, 1573-8.

Zhang, X., Jafari, N., Barnes, R. B., Confino, E., Milad, M., Kazer, R. R. (2005) Studies of gene expression in human cumulus cells indicate pentraxin 3 as a possible marker for oocyte quality. Fertil Steril, 83 Suppl 1, 1169-79.

Zheng D, Haddadin S, Wang Y, Gu L Q, Perry M C, Freter C E, Wang M X. (2011) Plasma microRNAs as novel biomarkers for early detection of lung cancer. Int J Clin Exp Pathol. 2011 Aug. 15; 4(6):575-86. Epub 2011 Aug. 8.

Zhu, X. M., Zhu, Y. M., Xu, C. M., Qian, Y. L., Jin, F., Huang, H. F. (2007) Autologous mature follicular fluid: its role in in vitro maturation of human cumulus-removed oocytes. Fertil Steril.

The invention claimed is:

1. A method of implanting an embryo in a female undergoing in vitro fertilization, comprising the steps of:
  a) collecting at least one oocyte with its cumulus cells from said female;
  b) measuring, in said cumulus cells surrounding said oocyte, an expression level of each of the 5 microRNA hsa-let-7a-1, hsa-mir-182, hsa-mir-21, hsa-mir-320a and hsa-mir-210;
  c) comparing the expression level of each of the 5 microRNA in the cumulus cells with control expression levels of the 5 microRNA from cumulus cells associated with competent oocytes;
  d) assessing said oocyte as having a higher probability of being competent if the 5 microRNA are not differentially expressed when compared to cumulus cells associated with competent oocytes;
  e) fertilizing said oocyte having a higher probability of being competent in vitro to generate an embryo; and
  f) implanting said embryo in said female.

2. The method according to claim 1, further comprising a step of measuring in the cumulus cells surrounding said oocyte the expression level of one or more genes selected from the group consisting of ATF3, SIAT6, PRKACA, PLA2G5, GPC6, GOS2, RBMS1, NFIC, SLC40A1 and WNT6.

3. A method of implanting an embryo in a female undergoing in vitro fertilization, comprising the steps of:
  a) collecting oocytes from said female;
  b) generating embryos from said oocytes by fertilizing said oocytes in vitro;
  c) measuring, in cumulus cells surrounding each of said embryos, an expression level of each of the 5 microRNA hsa-let-7a-1, hsa-mir-182, hsa-mir-21, hsa-mir-320a and hsa-mir-210;

c) comparing the expression level of each of the 5 microRNA in the cumulus cells with control expression levels of the 5 microRNA from cumulus cells associated with a competent embryo;

d) assessing said embryo as having a higher probability of being competent if the 5 microRNA are not differentially expressed when compared to cumulus cells associated with a competent embryo;

f) implanting said embryo having a higher probability of being competent in said female.

4. The method according to claim 3, further comprising a step of measuring in the cumulus cells surrounding said embryo the expression level of one or more genes selected from the group consisting of ATF3, SIAT6, PRKACA, PLA2G5, GPC6, GOS2, RBMS1, NFIC, SLC40A1 and WNT6.

5. A method of implanting an embryo in a female undergoing in vitro fertilization, comprising the steps of:

a) collecting at least one oocyte with its cumulus cells from said female;

b) culturing said cumulus cells having surrounded said oocyte on an adapted culture medium;

c) measuring, in said culture medium, an expression level of each of the 5 microRNA hsa-let-7a-1, hsa-mir-182, hsa-mir-21, hsa-mir-320a and hsa-mir-210;

d) comparing the expression level of each of the 5 microRNA in the culture medium with control expression levels of the 5 microRNA from culture media of cumulus cells associated with competent oocytes;

d) assessing said oocyte as having a higher probability of being competent if the 5 microRNA are not differentially expressed when compared to culture media of cumulus cells associated with a competent oocytes;

e) fertilizing said oocyte having a higher probability of being competent in vitro to generate an embryo; and f) implanting said embryo in said female.

* * * * *

SEQUENCE LISTING

```
<160> NUMBER OF SEQ ID NOS: 25

<210> SEQ ID NO 1
<211> LENGTH: 26
<212> TYPE: RNA
<213> ORGANISM: Artificial Sequence
<220> FEATURE:
<223> OTHER INFORMATION: Synthetic oligonucleotide adapter sequence

<400> SEQUENCE: 1
guucagaguu cuacaguccg acgauc                                          26

<210> SEQ ID NO 2
<211> LENGTH: 22
<212> TYPE: RNA
<213> ORGANISM: Artificial Sequence
<220> FEATURE:
<223> OTHER INFORMATION: Synthetic oligonucleotide adaptersequence

<400> SEQUENCE: 2
ucguaugccg ucuucugcuu gu                                              22

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 3
caagcagaag acggcatacg a                                               21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 4
```
caagcagaag acggcatacg a    21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
aatgatacgg cgaccaccga    20

<210> SEQ ID NO 6
<211> LENGTH: 28
<212> TYPE: RNA
<213> ORGANISM: Homo sapiens

<400> SEQUENCE: 6
agaaggaacg ucuggaguuu gugcuggu    28

<210> SEQ ID NO 7
<211> LENGTH: 26
<212> TYPE: RNA
<213> ORGANISM: Homo sapiens

<400> SEQUENCE: 7
guuuauucua gagagaauuc uuacuc    26

<210> SEQ ID NO 8
<211> LENGTH: 19
<212> TYPE: RNA
<213> ORGANISM: Homo sapiens

<400> SEQUENCE: 8
agacuuucgg ccuaggauc    19

<210> SEQ ID NO 9
<211> LENGTH: 19
<212> TYPE: RNA
<213> ORGANISM: Homo sapiens

<400> SEQUENCE: 9
agguucuguc guaucaauc    19

<210> SEQ ID NO 10
<211> LENGTH: 19
<212> TYPE: RNA
<213> ORGANISM: Homo sapiens

<400> SEQUENCE: 10
cgagccgggc ccuuccguc    19

<210> SEQ ID NO 11
<211> LENGTH: 19
<212> TYPE: RNA
<213> ORGANISM: Homo sapiens

<400> SEQUENCE: 11
cggaaaggag ggaaagggc    19

<210> SEQ ID NO 12
<211> LENGTH: 19
<212> TYPE: RNA
<213> ORGANISM: Homo sapiens

```
<400> SEQUENCE: 12
cgggcggaga guaggcauc                                                    19

<210> SEQ ID NO 13
<211> LENGTH: 19
<212> TYPE: RNA
<213> ORGANISM: Homo sapiens

<400> SEQUENCE: 13
guggagccgg gcguggacu                                                    19

<210> SEQ ID NO 14
<211> LENGTH: 19
<212> TYPE: RNA
<213> ORGANISM: Homo sapiens

<400> SEQUENCE: 14
cucuucgucu gucccuauc                                                    19

<210> SEQ ID NO 15
<211> LENGTH: 19
<212> TYPE: RNA
<213> ORGANISM: Homo sapiens

<400> SEQUENCE: 15
uccaucaaag aucggcauc                                                    19

<210> SEQ ID NO 16
<211> LENGTH: 19
<212> TYPE: RNA
<213> ORGANISM: Homo sapiens

<400> SEQUENCE: 16
ugugggaaga gggcauccu                                                    19

<210> SEQ ID NO 17
<211> LENGTH: 19
<212> TYPE: RNA
<213> ORGANISM: Homo sapiens

<400> SEQUENCE: 17
aggagcaaga gggcauccu                                                    19

<210> SEQ ID NO 18
<211> LENGTH: 19
<212> TYPE: RNA
<213> ORGANISM: Homo sapiens

<400> SEQUENCE: 18
gcgaggcacu guggagauc                                                    19

<210> SEQ ID NO 19
<211> LENGTH: 19
<212> TYPE: RNA
<213> ORGANISM: Homo sapiens

<400> SEQUENCE: 19
aggcagguga aggcauccu                                                    19

<210> SEQ ID NO 20
<211> LENGTH: 19
```

```
<212> TYPE: RNA
<213> ORGANISM: Homo sapiens

<400> SEQUENCE: 20
ugggaucccg aggcauccu                                                   19

<210> SEQ ID NO 21
<211> LENGTH: 25
<212> TYPE: RNA
<213> ORGANISM: Homo sapiens

<400> SEQUENCE: 21
gcagaucuuc cuggguggug uggac                                            25

<210> SEQ ID NO 22
<211> LENGTH: 19
<212> TYPE: RNA
<213> ORGANISM: Homo sapiens

<400> SEQUENCE: 22
gguagugucg cgggggugc                                                   19

<210> SEQ ID NO 23
<211> LENGTH: 19
<212> TYPE: RNA
<213> ORGANISM: Homo sapiens

<400> SEQUENCE: 23
aaggacugug aucauugaa                                                   19

<210> SEQ ID NO 24
<211> LENGTH: 19
<212> TYPE: RNA
<213> ORGANISM: Homo sapiens

<400> SEQUENCE: 24
agcgacguuu cauugaaaa                                                   19

<210> SEQ ID NO 25
<211> LENGTH: 19
<212> TYPE: RNA
<213> ORGANISM: Homo sapiens

<400> SEQUENCE: 25
gggggcugua ucauugaca                                                   19
```